United States Patent [19]

Bonnet et al.

[11] Patent Number: 4,561,438
[45] Date of Patent: Dec. 31, 1985

[54] PIEZOELECTRIC TRANSDUCER WITH CURVED SHAFTS

[75] Inventors: Ludwig Bonnet, Knittlingen; Ehrenfried Bitrolf, Bretten-Ruit, both of Fed. Rep. of Germany

[73] Assignee: Richard Wolf GmbH, Knittlingen, Fed. Rep. of Germany

[21] Appl. No.: 682,474

[22] Filed: Dec. 17, 1984

Related U.S. Application Data

[63] Continuation of Ser. No. 472,009, Mar. 4, 1983, abandoned.

[30] Foreign Application Priority Data

Mar. 4, 1982 [DE] Fed. Rep. of Germany ... 8205955[U]

[51] Int. Cl.$^4$ .............................................. A61B 17/00
[52] U.S. Cl. .................................. 128/328; 128/24 A; 604/22
[58] Field of Search ............... 604/22; 285/332.1, 258; 433/118–119, 142; 318/116, 118; 336/127, 600; 310/26, 323, 325; 128/328, 24 A, 303 R, 305

[56] References Cited

U.S. PATENT DOCUMENTS

| Re. 28,752 | 3/1976  | Balamuth et al. | 318/116 |
| 2,863,678  | 12/1958 | Gordon et al.   | 285/332.1 |
| 2,878,809  | 3/1959  | Treace          | 128/303 R |
| 3,352,303  | 11/1967 | Delaney         | 604/22 |
| 3,433,226  | 3/1969  | Boyd            | 128/305 |
| 3,518,766  | 1/1970  | Burt            | 433/119 |
| 3,693,613  | 9/1972  | Kelman          | 128/24 A |
| 3,956,826  | 5/1976  | Perdreaux, Jr.  | 128/24 A |
| 4,168,447  | 9/1979  | Bussiere et al. | 310/323 |
| 4,169,984  | 10/1979 | Parisi          | 128/24 A |
| 4,526,571  | 7/1985  | Wuchinich       | 604/22 |

FOREIGN PATENT DOCUMENTS

| 2724324 | 8/1978 | Fed. Rep. of Germany | 128/328 |
| 2032221 | 4/1980 | United Kingdom       | 310/323 |

*Primary Examiner*—C. Fred Rosenbaum
*Assistant Examiner*—Gene B. Kartchner
*Attorney, Agent, or Firm*—Hill, Van Santen, Steadman & Simpson

[57] ABSTRACT

This invention relates to a piezoelectric transducer for generating ultrasonic oscillations, in which a bolt joining two metal elements clamping the transducer elements is constructed as a flushing passage, and to which a curved tubular shaft is connected via an end fitting comprising a passage. The shaft has its internal diameter enlarged as far as beyond the area of its curvature, and the bolt is traversed on the one hand by a plastics material tube connectible to the end fitting and may be connected at the proximal side of the transducer to a flushing pipe.

3 Claims, 2 Drawing Figures

PIEZOELECTRIC TRANSDUCER WITH CURVED SHAFTS

This is a continuation of application Ser. No. 472,009, filed Mar. 4, 1983, now abandoned.

BACKGROUND OF THE INVENTION

The present invention relates to piezoelectric transducers for generating ultrasonic oscillations for disintegrating bladder, urethra and kidney stones, of the kind which comprises two piezoelectric discs clamped between two metal elements by means of a tubular bolt utilizable as a flushing passage, and whereof the metal element at the distal side may have a curbed tubular shaft transmitting the ultrasonic oscillations and joined to the flushing passage of the bolt screwed to it via an end fitting provided with a passage.

In known transducers of the kind referred to above, the shaft transmitting the ultrasonic oscillations, which has a curvilinear portion and acts as a flushing passage, had a comparatively small internal diameter along the area of curvature, and the flushing passage extending through the transducer comprises a rigid duct pipe connected to the transmitting element on the one hand, and to a flushing pipe on the other hand. It was discovered that the shaft used as a transmitter element tends to fracture in the area of the curvilinear portion and in the transition to the end fitting due to the longitudinal and transverse effects of the ultrasonic oscillations caused by the curvature, and that the oscillation conditions, and in particular the efficiency of power transmission, are effected deleteriously by the rigid pipe passing through the transducer. Moreover, the particles of material produced by disintegration of stones and intended to be extracted, rapidly settled, primarily within the passage extending through the transducer, so that fluid draining was no longer assured.

Consequently, it is an object of the invention to reduce or eliminate the tendency of the tubular shaft transmitting the ultrasonic oscillations to the stone which is to be broken up, to fracture in the area of the curvature and in draining the flushing fluid together with the matter to be removed in unobjectionable manner, without obstruction by the sonic oscillator.

SUMMARY OF THE INVENTION

In the case of a transducer as hereinabove referred to, this problem is resolved in that the proximal part of the shaft has an enlarged internal diameter as far as beyond the area of its curvature and continues in cylindrically constricted form up to the distal shaft extremity, and in that the plastics material tube traversing the bolt is connected at one side to the end fitting by a clamping joint and at the other and proximal side of the transducer to a flushing pipe via another clamping joint.

Due to the increase in the internal diameter of the proximal shaft section incorporating the area of curvature, this area will incur lesser strain from the oscillation components in the transverse direction, so that the risk of fracture in this area is reduced decisively. Because the flushing passage extending through the transducer consists of a plastics material tube, the oscillations engendered may be absorbed resiliently and deleterious actions remain ineffective as regards the oscillation conditions, so that the power as a whole may be transmitted to the stone. Clogging of the flushing passage is moreover substantially avoided.

BRIEF DESCRIPTION OF THE DRAWINGS

In order that the invention may be more clearly understood reference will now be made to the accompanying drawings illustrating one embodiment thereof by way of example and in which.

DETAILED DESCRIPTION OF THE PREFERRED EMBODIMENT

Figure 1:
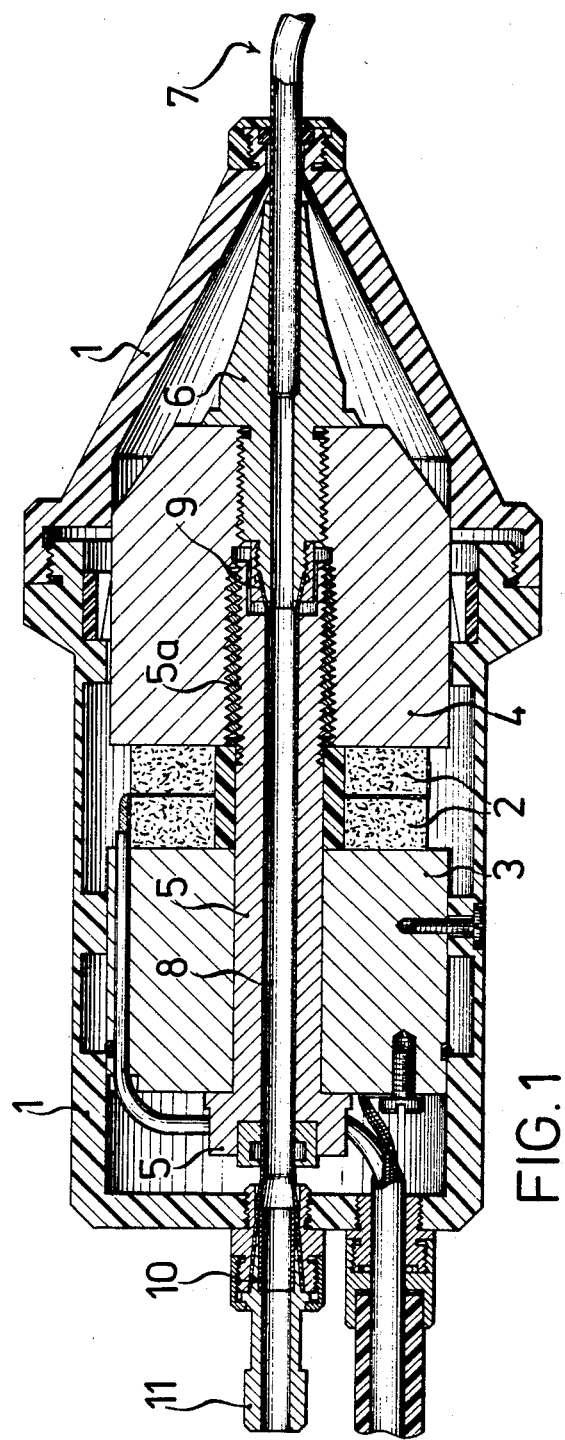
FIG. 1 shows an axial cross-section through a piezoelectric transducer comprising the shaft transmitting the ultrasonic oscillations, and the flushing passage connected proximally to the shaft and extending through the transducer.
Figure 2:
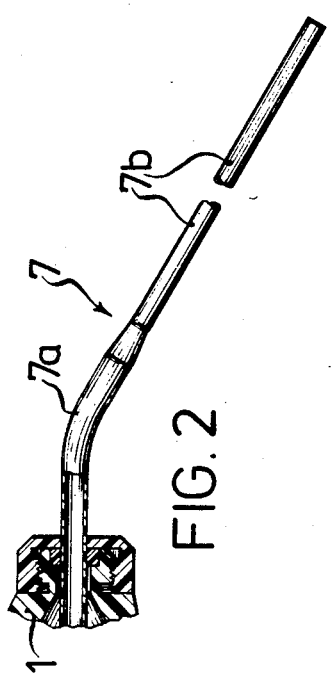
FIG. 2 shows a side view of the shaft transmitting the ultrasonic oscillations and intended to be connected to the transducer according to FIG. 1, and forming a continuation of that Figure.

Referring now to the drawings the piezoelectric transducer per se, intended to generate ultrasonic oscillations for disintegrating kidney stones or the like, is known per se. In the casing 1, two piezoelectric discs 2 are clamped between the metal elements 3 and 4 by means of a bolt 5 provided with an axial passage, which is screwed with a screwthread 5a into the metal element 4 at the distal side. Into this metal element 4 is also screwed an end fitting 6 having an axial passage, wherein is connected a brazed-in shaft joined to the passage and provided with a curvilinear portion 7a, the internal diameter of which is enlarged within the section of the end fitting 6 and as far as beyond the curved portion 7a and thereafter continues in cylindrically constricted manner up to the distal extremity 7b.

The passage of the bolt 5 is traversed by a plastics material tube 8, for example a material known under the trade mark "Teflon", the distal extremity of which is clamped at 9 between a hollow cone and a mating cone of the end fitting 6 screwable into the former, and the proximal extremity of which, led out of the casing 1, is clamped at 10 within a coupling element also comprising a hollow cone and mating cone, and is connected to a flushing pipe 11.

We claim:

1. A piezoelectric transducer for generating ultrasonic oscillations for disintegrating bladder, urethra and kidney stones, of the kind which comprises two piezoelectric discs clamped between two metal elements by means of a tubular bolt utilizable as a flushing passage, and whereof the metal element at the distal side has a curved tubular shaft transmitting the ultrasonic oscillations and joined to the flushing passage of the bolt screwed to it via an end fitting provided with a passage, wherein the proximal part of said shaft has an enlarged internal diameter as far as the area of its curvature and continues from the latter to the distal extremity whilst constricted cylindrically, and wherein the bolt is traversed by a plastics material tube which is joined at one end to the end fitting via a clamping joint and is connected at the other end at the proximal side of the transducer to a flushing pipe via another clamping joint.

2. A piezoelectric transducer as claimed in claim 1, wherein the clamping joints each comprise a hollow cone and a mating cone receiving a tube extremity between them and secured by being screwed together.

3. A piezoelectric transducer for generating ultrasonic oscillations for disintegrating bladder, urethra, and kidney stones comprising:

a housing having a distal end and a proximal end;

two piezoelectric discs clamped between two metal elements in said housing by a tubular bolt, said tubular bolt terminating within one of said metal elements closer to said distal end;
a plastic sleeve extending through said tubular bolt forming a flushing passage;
an end fitting mating in said housing at said distal end with said one metal element, said end fitting having a passage communicating with said flushing passage;
a hollow shaft for transmitting said ultrasonic oscillations and for flushing, said shaft having a first cylindrical portion of a first diameter which is received in said passage in said end fitting and which is curved near said distal end of said housing, having a second cylindrical portion of a second diameter less than said first diameter, said second cylindrical portion being straight, and having a frusto-conical transition section joining said first and second cylindrical portions; and
a clamping joint at said proximal end of said housing for joining said plastic sleeve to an external flushing pipe.

* * * * *